United States Patent
Kurihara et al.

(10) Patent No.: US 11,253,818 B2
(45) Date of Patent: Feb. 22, 2022

(54) METHOD FOR PRODUCING CELLULASE AND APPARATUS FOR SAID METHOD

(71) Applicant: Toray Industries, Inc., Tokyo-to (JP)

(72) Inventors: Hiroyuki Kurihara, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 985 days.

(21) Appl. No.: 14/359,122

(22) PCT Filed: Nov. 21, 2012

(86) PCT No.: PCT/JP2012/080123
§ 371 (c)(1),
(2) Date: May 19, 2014

(87) PCT Pub. No.: WO2013/077341
PCT Pub. Date: May 30, 2013

(65) Prior Publication Data
US 2014/0295525 A1 Oct. 2, 2014

(30) Foreign Application Priority Data

Nov. 21, 2011 (JP) .............................. JP2011-253706

(51) Int. Cl.
*B01D 61/18* (2006.01)
*C12M 1/00* (2006.01)
(Continued)

(52) U.S. Cl.
CPC .......... *B01D 61/18* (2013.01); *B01D 61/142* (2013.01); *B01D 61/145* (2013.01); *B01D 61/16* (2013.01);
(Continued)

(58) Field of Classification Search
CPC .... B01D 61/18; B01D 61/142; C12N 9/2437; C12R 2001/885; C12Y 302/01004
See application file for complete search history.

(56) References Cited

U.S. PATENT DOCUMENTS

| 4,725,544 A | 2/1988 | Tan et al. |
| 5,811,381 A | 9/1998 | Emalfarb et al. |

(Continued)

FOREIGN PATENT DOCUMENTS

| JP | 01-309683 A | 12/1989 |
| JP | 11-513885 A | 11/1999 |

(Continued)

OTHER PUBLICATIONS

NPL document "Ultrafiltration Fundamentals" obtained at https://laboratory.pall.com/content/dam/pall/laboratory/literature-library/non-gated/Ultrafiltration%20Fundamentals%20.pdf, accessed Jun. 9, 2017, online since Feb. 1, 2002 according to Google.*

(Continued)

*Primary Examiner* — David W Berke-Schlessel
*Assistant Examiner* — Trent R Clarke
(74) *Attorney, Agent, or Firm* — DLA Piper LLP (US)

(57) ABSTRACT

A method of producing cellulase includes steps (1) to (3): (1) subjecting an aqueous solution of cellulase derived from filamentous fungi to filtration through an ultrafiltration membrane with a molecular weight cut off of 100,000 to 200,000 to obtain a filtrate and concurrently obtain a concentrated enzyme liquid as a retentate; (2) further subjecting the filtrate obtained in step (1) to filtration through a second ultrafiltration membrane with a molecular weight cut off of 5,000 to 50,000 to obtain a second concentrated enzyme liquid as a retentate; and (3) mixing the concentrated enzyme liquid obtained in steps (1) and (2) to obtain cellulase derived from filamentous fungi.

18 Claims, 5 Drawing Sheets

(51) Int. Cl.
  *C12P 21/00* (2006.01)
  *B01D 61/16* (2006.01)
  *B01D 61/14* (2006.01)
  *C12N 9/42* (2006.01)

(52) U.S. Cl.
  CPC ............ *C12M 21/14* (2013.01); *C12M 47/10* (2013.01); *C12N 9/2437* (2013.01); *C12P 21/00* (2013.01); *B01D 2311/2688* (2013.01); *B01D 2317/025* (2013.01); *B01D 2317/027* (2013.01)

(56) References Cited

U.S. PATENT DOCUMENTS

| | | | |
|---|---|---|---|
| 6,190,898 B1 | 2/2001 | Becker et al. | |
| 2010/0190965 A1 | 7/2010 | Yamaguchi et al. | |
| 2013/0059345 A1* | 3/2013 | Kurihara | C12P 19/14 435/99 |

FOREIGN PATENT DOCUMENTS

| | | | | |
|---|---|---|---|---|
| JP | 2001-506845 A | 5/2001 | | |
| JP | 2009-240167 A | 10/2009 | | |
| JP | 2010-051927 A | 3/2010 | | |
| JP | 2010-221136 A | 10/2010 | | |
| JP | WO 2011115039 A1 * | 9/2011 | ............. | C12P 19/14 |
| WO | 2007/034999 A1 | 3/2007 | | |
| WO | 2008/156124 A1 | 12/2008 | | |
| WO | 2011/019686 | 2/2011 | | |
| WO | 2011/115040 A1 | 9/2011 | | |

OTHER PUBLICATIONS

Notification of Reasons for Refusal dated Oct. 18, 2016, of corresponding Japanese Application No. 2012-554153 with an English translation.

Supplementary European Search Report dated Jun. 11, 2015 of corresponding European Application No. 12852032.7.

J. Wang, et al., "Purification of Cellulose Using Ultrafiltration," *Journal of Biotechnology*, Elsevier Science Publishers, vol. 150, Nov. 1, 2010, p. 388.

W. Mores, et al., "Cellulose Recovery Via Membrane Filtration," *Applied Biochemistry and Biotechnology*, Humana Press, Inc., vol. 91-93, Apr. 1, 2001, pp. 297-309.

R. Henley, et al., "Enzymatic saccharification of cellulose in membrane reactors," *Enzyme and Microbial Technology*, vol. 2, No. 3, Jul. 1, 1980, pp. 206-208.

Chinese First Office Action of corresponding Chinese Application No. 201280057111.5 dated Feb. 10, 2015 with English translation.

* cited by examiner

METHOD FOR PRODUCING CELLULASE AND APPARATUS FOR SAID METHOD

TECHNICAL FIELD

This disclosure relates to a method of producing cellulase by membrane separation and concentration of a cellulase component derived from filamentous fungi and a device therefor.

BACKGROUND

Polysaccharides such as starch or cellulose are available as biomass resources. A method of producing monosaccharides such as glucose or xylose by enzymatically hydrolyzing such polysaccharides has been known. The sugar liquid obtained by breaking down such polysaccharides is widely used as carbon sources in microorganism culture. In particular, as an enzyme that hydrolyzes cellulose, cellulase is known. As microorganisms that produce this cellulase, filamentous fungi are known. The filamentous fungi produce a large amount of cellulases as extracellular enzymes by setting up culture conditions to inductively produce the cellulase. As these filamentous fungi, available are filamentous fungi such as the genus *Aspergillus*, the genus *Humicola*, the genus *Mucor*, the genus *Trichoderma*, and the genus *Acremonium*, which are widely used in production of cellulase.

Enzyme components that exhibit various substrate specificities are present in cellulase derived from filamentous fungi. Specifically, present are cellobiohydrolase that acts on the crystalline region of cellulose, endoglucanase that acts from within cellulose molecular chain to reduce the molecular weight thereof, β-glucosidase that acts on water-soluble oligosaccharides or cellobiose, and hemicellulase that acts on hemicellulose. It has been known that each of these enzyme components with varied substrate specificity acts synergistically on cellulose fibers and thereby efficient degradation of cellulose is taken place (see Encyclopedia of Cellulose, Chapter 6, Biodegradation of Cellulose (edited by The Cellulose Society of Japan, 2000)). It has also been known that, in such a cellulase derived from filamentous fungi, each of the enzyme components whose molecular weight varies in size from small to large is present, wherein the molecular weight ranges from 20 to 100 kDa.

With regard to cellulase derived from filamentous fungi, methods of membrane separation and concentration using an ultrafiltration membrane in the same manner as common enzymes are known. For instance, methods of separation and recovery of cellulases using an ultrafiltration membrane have been known, which method comprises membrane separation and concentration of cellulases from a culture of microorganisms such as filamentous fungi or a cellulose hydrolysate obtained by using the cellulase (see WO 2007/034999 and Japanese Patent Application Laid-Open Publication Nos. 2010-221136 and 2009-240167). As a treatment prior to the step of the membrane separation and concentration through such an ultrafiltration membrane, methods have been suggested, which method comprises removing in advance solids contained in an aqueous solution of cellulase from a microorganism culture or cellulose hydrolysate by use of, for example, a ceramic spin filter (see JP '136) or a non-woven fabric with a pore diameter of 20 to 200 µm (see JP '167). Yet, for the membrane separation and concentration of each of the cellulase components, it has been common to use an ultrafiltration membrane having a fine pore diameter or molecular weight cut off that sufficiently blocks molecular weight corresponding to the cellulase component to be recovered.

In the membrane separation and concentration of filamentous fungi cellulase using a conventional ultrafiltration membrane, problems have included fouling of the ultrafiltration membrane and inactivation or aggregation of the cellulase component. These problems have caused a filtration treatment speed of the ultrafiltration membrane to become slower or have caused a cellulase activity obtained by the ultrafiltration membrane to become lower, which has been also problematic.

In view of this, it could be helpful to provide a method of efficient membrane separation and concentration of cellulase components derived from *Trichoderma* by using an ultrafiltration membrane and to provide a device therefor.

SUMMARY

We thus provide:

[1] A method of producing cellulase comprising the following steps of (1) to (3):
   (1) the step of subjecting an aqueous solution of cellulase derived from filamentous fungi to filtration through an ultrafiltration membrane with a molecular weight cut off of 100,000 to 200,000 to obtain a filtrate and to concurrently obtain a concentrated enzyme liquid as a retentate;
   (2) the step of further subjecting the filtrate obtained in step (1) to filtration through a second ultrafiltration membrane with a molecular weight cut off of 5,000 to 50,000 to obtain a second concentrated enzyme liquid as a retentate; and
   (3) the step of mixing the concentrated enzyme liquid obtained in steps (1) and (2) to obtain cellulase derived from filamentous fungi.

[2] The method of producing cellulase according to [1], wherein the filamentous fungi is *Trichoderma*.

[3] The method of producing cellulase according to [1] or [2], wherein the aqueous solution of cellulase derived from filamentous fungi is adjusted to pH 2.6 to 5.4 or pH 8.6 to 9.4 in step (1).

[4] The method of producing cellulase according to any of [1] to [3], wherein the aqueous solution of cellulase derived from filamentous fungi is a filamentous fungi culture liquid or a hydrolysate of biomass containing cellulose obtained by using the cellulase derived from filamentous fungi.

[5] The method of producing cellulase according to any of [1] to [4], wherein the aqueous solution of cellulase derived from filamentous fungi comprises one or more enzyme components selected from the group consisting of cellobiohydrolase, endoglucanase, and xylanase.

[6] The method of producing cellulase according to any of [1] to [5], wherein a temperature of the aqueous solution of cellulase derived from filamentous fungi is in a temperature range of 15 to 35° C.

[7] A device of producing cellulase comprising a tank for an aqueous solution of cellulase, an ultrafiltration pump that is connected therewith, and at least one of an ultrafiltration membrane with a molecular weight cut off of 100,000 to 200,000 that are connected in series or in parallel, a holding tank for a filtrate of the above-mentioned ultrafiltration membrane, a second ultrafiltration membrane with a molecular weight cut off of 5,000 to 50,000, and a second holding tank for a concentrated enzyme liquid.

[8] The device of producing cellulase according to [7], wherein the tank for an aqueous solution of cellulase comprises a pH sensor and is further connected with a pH adjuster tank.

It is possible to efficiently carry out membrane separation and concentration of cellulase components from an aqueous solution of cellulase derived from filamentous fungi. Specifically, part of cellulase components derived from filamentous fungi can be separated and recovered in step (1) and further the remaining cellulase component derived from filamentous fungi contained in a filtrate can be recovered in step (2), thereby recovering a notably high Avicel degrading activity.

DESCRIPTION OF SYMBOLS

Figure 1:
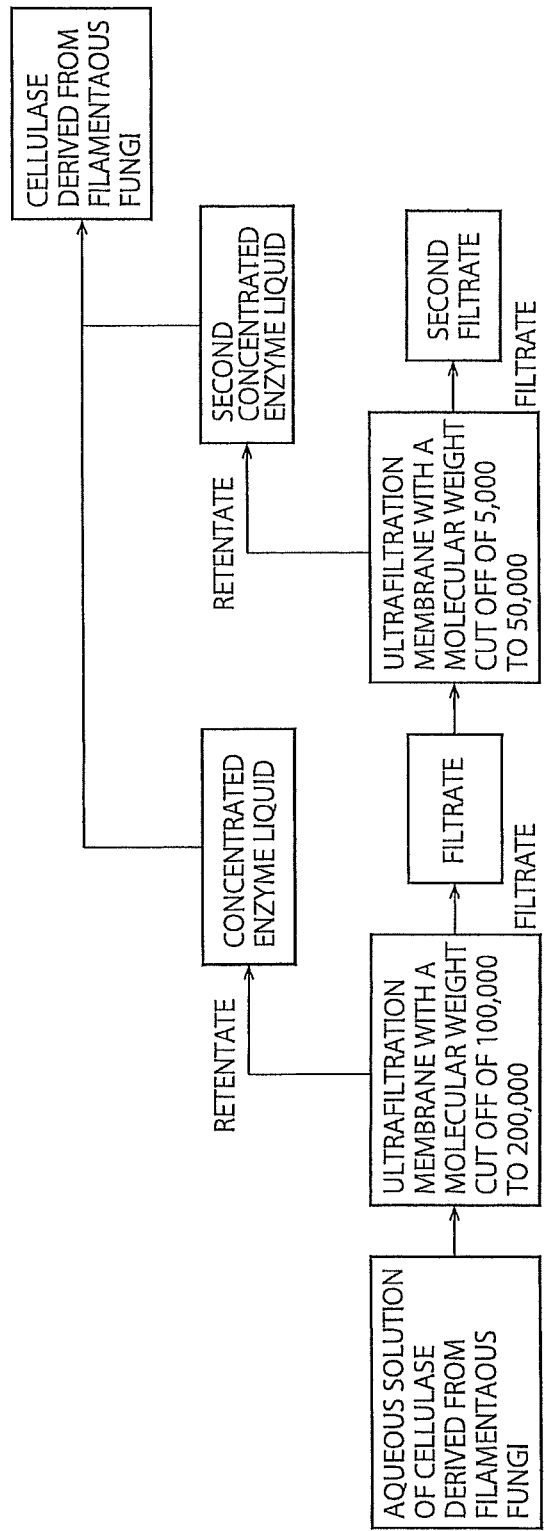
FIG. 1 is a drawing showing a flow of the steps of the method of producing cellulase.

1 Tank for an aqueous solution of cellulase
2 pH sensor
3 pH adjuster tank
4 pH adjustment pump
5 Valve
6 Ultrafiltration pump 1
7 Compressor
8 Ultrafiltration membrane with a molecular weight cut off of 100,000 to 200,000
9 Backwash pump
10 Holding tank for filtrate
11 Valve 2
12 Ultrafiltration pump 2
13 Ultrafiltration membrane with a molecular weight cut off of 5,000 to 50,000
14 Second holding tank for filtrate
14 Second holding tank for concentrated enzyme liquid

DETAILED DESCRIPTION

The method of producing cellulase is composed of the steps comprising the following steps of (1) to (3) as shown in FIG. 1.

Step (1)

In step (1), an aqueous solution of cellulase derived from filamentous fungi is subjected to filtration through an ultrafiltration membrane with a molecular weight cut off of 100,000 to 200,000 to obtain a filtrate and at the same time to obtain a concentrated enzyme liquid as a retentate. It was found out that, on this occasion, a part of the enzyme components contained in the aqueous solution of cellulase derived from filamentous fungi was separated as the retentate of the ultrafiltration membrane with a molecular weight cut off of 100,000 to 200,000. Further, on the other hand, we discovered that, also in the feed side, the remaining enzyme component is separated in the feed side; and the remaining enzyme component is recovered in step (2).

Step (2)

In step (2), the filtrate of the above-mentioned step (1) is further subjected to filtration through the second ultrafiltration membrane with a molecular weight cut off of 5,000 to 50,000 to obtain the second concentrated enzyme liquid as a retentate. By this, it is possible to fully recover the enzyme component that is contained in the filtrate of step (1). Separation and concentration of cellulase derived from filamentous fungi in two steps of the ultrafiltration membrane with a molecular weight cut off of 100,000 to 200,000 in the above-described step (1) and the ultrafiltration membrane with a molecular weight cut off of 5,000 to 50,000 in step (2) enables a higher enzyme activity to be separated, as compared with a conventional technique comprising the separation and concentration solely using the ultrafiltration membrane with a molecular weight cut off of 5,000 to 50,000.

Step (3)

In step (3), the first concentrated enzyme liquid obtained in step (1) and the second concentrated enzyme liquid obtained in step (2) are mixed to obtain a cellulase having a high enzyme activity from the aqueous solution of cellulase derived from filamentous fungi. The cellulase obtained in step (3) can be used as is. Yet, it may be used with the concentration or pH of cellulase being adjusted as appropriate.

A preferred example will be further described in detail below.

Cellulase derived from filamentous fungi refers to cellulase produced by filamentous fungi. Examples of filamentous fungi that produce the cellulase include microorganisms such as *Trichoderma, Aspergillus, Cellulomonas, Clostridium, Streptomyces, Humicola, Acremonium, Irpex, Mucor,* or *Talaromyces*. Because these microorganisms produce the cellulase in a culture liquid thereof, the culture liquid may be used as is as an unpurified filamentous fungi cellulase; or the culture liquid may be purified and formulated, and the formulated one may be used as a filamentous fungi cellulase.

Cellulase derived from filamentous fungi is preferably cellulase derived from *Trichoderma*. *Trichoderma* refers to filamentous fungi that are classified in the genus *Trichoderma*, the genus *Humicola*, and the genus *Hypocrea*. Further, cellulase derived from *Trichoderma* refers to the whole of cellulase components that are intracellularly or extracellularly produced by the above-mentioned *Trichoderma*. In addition, the cellulase refers to both an enzyme having a hydrolysis activity of cellulose and an enzyme having a hydrolysis activity of hemicellulose.

Further, among cellulase derived from *Trichoderma*, more preferred is cellulase derived from *Trichoderma reesei*. Examples of the cellulase derived from *Trichoderma reesei* include cellulase derived from *Trichoderma reesei* QM9414, *Trichoderma reesei* QM9123, *Trichoderma reesei* RutC-30, *Trichoderma reesei* PC3-7, *Trichoderma reesei* ATCC66589, *Trichoderma reesei* CL-847, *Trichoderma reesei* MCG77, and *Trichoderma reesei* MCG80. Further, a mutant strain with an improved cellulase productivity may be used, which mutant strain is derived from the above-described *Trichoderma* and obtained by subjecting the bacterial strain to mutagenesis by a mutagen, irradiation with UV, or the like.

Because various cellulases are secreted and produced in a culture liquid by culturing *Trichoderma* under appropriate medium conditions, it is possible to obtain cellulase derived from *Trichoderma* from such a culture liquid. Such a culture liquid may remain unpurified and be used as cellulase derived from *Trichoderma*; or the culture liquid may be one that is purified or further formulated by a known technique. In cases where cellulase derived from *Trichoderma* is purified from the above-mentioned culture liquid and used as one that has been formulated, it may be one added with substances other than the enzyme such as protease inhibitors, dispersants, dissolution accelerants, and stabilizers.

Further, the cellulase derived from *Trichoderma* may be one obtained by adjusting DNA coding for an amino acid sequence of a cellulase component present on the *Trichoderma* genome, linking the resulting DNA to an expression vector, and introducing this expression vector in a host to produce a recombinant protein, followed by isolation and purification thereof.

*Trichoderma* produce at least two kinds of endoglucanases (endoglucanase I, endoglucanase II), at least two kinds of cellobiohydrolases (cellobiohydrolase I, cellobiohydrolase II), at least two kinds of hemicellulases (xylanase, xylosidase), and one or more kinds of β-glucosidases.

Cellobiohydrolase is a general term for cellulases characterized by hydrolyzing cellulose from the terminal portions. The group of enzymes belonging to cellobiohydrolase is described as EC number: EC3.2.1.91. Endoglucanase is a general term for cellulases characterized by hydrolyzing cellulose molecular chains from their central portions. The group of enzymes belonging to endoglucanase is described as EC number: EC3.2.1.4. Exoglucanase is a general term for cellulases characterized by hydrolyzing cellulose molecular chains from their termini. The group of enzymes belonging to exoglucanase is described as EC number: EC3.2.1.74. β-glucosidase is a general term for cellulases characterized by acting on cellooligosaccharides or cellobiose. The group of enzymes belonging to β-glucosidase is described as EC number: EC3.2.1.21.

Xylanase is a general term for cellulases characterized by acting on hemicellulose or, in particular, xylan. The group of enzymes belonging to xylanase is described as EC number: EC3.2.1.8. Xylosidase is a general term for cellulases characterized by acting on xylooligosaccharides. The group of enzymes belonging to xylosidase is described as EC number: EC3.2.1.37.

The cellulase derived from filamentous fungi may be one in which a particular enzyme activity is enhanced by adding cellulase components from different species of microorganisms. What may be added is cellulase derived from filamentous fungi including, for example, the genus *Aspergillus*, the genus *Cellulomonas*, the genus *Clostridium*, the genus *Streptomyces*, the genus *Acremonium*, the genus *Irpex*, the genus *Mucor*, and the genus *Talaromyces*. Further, examples of thermophiles include microorganisms such as the genus *Sulofolobus*, the genus *Thermoplasma*, the genus *Caldivirgra*, the genus *Thermosphaera*, the genus *Pyrococcus*, the genus *Picrophilus*, the genus *Caldivirgra*, and the genus *Fervidobacterium*.

With regard to each of the enzyme components contained in cellulase derived from filamentous fungi, it is possible to specify the component thereof using a known separation technique. The identification can be carried out by, for example, separation via a known technique such as gel filtration, ion exchange, or two-dimensional electrophoresis, and amino acid sequence analysis (N-terminal analysis, C-terminal analysis, and mass spectrometry) of the separated component, followed by comparison to a database.

The enzyme activity of cellulase derived from filamentous fungi can be evaluated by the hydrolysis activity of polysaccharides including an Avicel degrading activity, carboxymethyl cellulose (CMC) degrading activity, cellobiose degrading activity, xylan degrading activity, and mannan degrading activity. With regard to the Avicel degrading activity, cellobiohydrolase or exoglucanase which has characteristics of hydrolyzing cellulose from the terminal portions is a principal enzyme exhibiting that activity. Further, with regard to the xylan degrading activity, xylanase and xylosidase are principal enzymes exhibiting that activity. With regard to the cellobiose degrading activity, β-glucosidase is mainly a principal enzyme exhibiting that activity. For CMC, all kinds of cellulase may exhibit a catalytic action. The term "principal" refers to an expression based on a fact that the enzyme is known to be most involved in the degradation. It means that enzyme components other than this principal one are also involved in the degradation.

An aqueous solution of cellulase derived from filamentous fungi is an aqueous solution that contains one or more kinds of cellulase components derived from the above-described filamentous fungi. It is to be noted that an aqueous solution that contains plural kinds of cellulase components derived from filamentous fungi is more preferred. Further, besides the intrinsic cellulase component derived from filamentous fungi, an enzyme or cellulase originated from different species of microorganisms may be contained.

The aqueous solution of cellulase derived from filamentous fungi is not in particular restricted. Preferred is a hydrolysate obtained by adding cellulase derived from filamentous fungi in a culture of filamentous fungi or biomass containing cellulose for hydrolysis. Examples of an acid used in pH adjustment include sulfuric acid, hydrochloric acid, acetic acid, phosphoric acid, and nitric acid. Examples of an alkali include sodium hydroxide, potassium hydroxide, and calcium hydroxide. The acid or alkali is not in particular restricted as long as it is capable of adjusting to a prescribed pH in an economical fashion and the enzyme components of cellulase derived from filamentous fungi are not inactivated or do not aggregate.

The aqueous solution of cellulase derived from filamentous fungi is preferably one that is subjected to one or more solid-liquid separation operations selected from centrifugation, filter press filtration, drum filter filtration, depth filter filtration, sedimentation separation, aggregation treatment, and sand filtration; and adjusted its turbidity to 0.1 to 100 NTU. Turbidity is defined in JIS K0101 "Testing Methods for Industrial Water" as follows: "Turbidity is an expression of a degree of the cloudiness of water and is sorted out into visual turbidity, transmitted light turbidity, scattered light turbidity, and integrating sphere turbidity to be indicated." When the measurement is carried out in comparison with a kaolin standard liquid, turbidity is expressed in "degrees (kaolin)" as a unit; whereas in cases where the measurement is carried out in comparison with a formazin standard liquid, turbidity is expressed in "degrees (formazin)" as a unit.

A formazin standard liquid which exhibits better reproducibility and stability than those of a kaolin standard liquid is used and the turbidity "NTU" which is measured by a scat-tered light measurement method is employed. NTU refers to "Nephelometric Turbidity Unit" and when the turbidity is more than 100 NTU, such a high turbidity becomes a factor for mem-brane fouling in filtration by an ultrafiltration membrane in step (2) described later. Therefore, it is preferred to adjust the turbidity to 0.1 to 100 NTU by carrying out the above-described one or more solid-liquid separation operations. The above-described solid-liquid separation technique can be carried out by a known device and procedure. In contrast, to adjust the turbidity to less than 0.1 NTU, it is required to use a microfiltration membrane with a fine pore diameter of 0.05 to 1.0 μm. In cases where such a microfiltration membrane is used, there is a possibility that the enzyme component of cellulase derived from filamentous fungi is blocked as a retentate of the microfiltration membrane and thus the turbidity is preferably 0.1 NTU or more.

The ultrafiltration membrane refers to a separation membrane having an average fine pore diameter of 0.02 to 0.0001 μm and a separation membrane capable of membrane separation and concentration of mainly water-soluble high molecular weight compounds such as enzymes or proteins via an effect of molecular sieving.

Two kinds of ultrafiltration membranes, which are the first ultrafiltration membrane with a molecular weight cut off of 100,000 to 200,000 and the second ultrafiltration membrane with a molecular weight cut off of 5,000 to 50,000, are used. Molecular weight cut off (MWCO) refers to one that defines the membrane performance by measuring the molecular weight that can be separated as a the retentate fraction of membrane, as is described that "A curve obtained by plotting data with the molecular weight of the solute along the horizontal axis and the blocking rate along the vertical axis is called a molecular weight cut off curve. The molecular weight at which the blocking rate is 90% is called the molecular weight cut off of the membrane." in The Membrane Society of Japan ed., Membrane Experiment Series, Vol. III, Artificial Membrane, editorial committee members: Shoji Kimura, Shin-ichi Nakao, Haruhiko Ohya, and Tsutomu Nakagawa (Kyoritsu Shuppan Co., Ltd., 1993), page 92. As for a technique of determining the molecular weight cut off, various dextran standard samples or protein standard samples whose molecular weight are known can be filtered through an ultrafiltration membrane to evaluate its blocking rate and draw a separation curve thereof, thereby determining the molecular weight cut off. Specifically, an ultrafiltration membrane with a molecular weight cut off of 100,000 refers to an ultrafiltration membrane that blocks 90% of the molecules with a molecular weight of 100,000.

Cellulase derived from filamentous fungi contains enzyme components varying in size from small to large at 20 to 100 kDa. When an aqueous solution of cellulase derived from filamentous fungi is subjected to filtration through the first ultrafiltration membrane with a molecular weight cut off of 100,000 to 200,000, it is expected that the enzyme component cannot be recovered from the feed side. However, contrary to expectations, in step (1), a part of the enzyme components in a range of 20 kDa to 100 kDa of cellulase derived from filamentous fungi can be recovered from the feed side by using the first ultrafiltration membrane with a molecular weight cut off of 100,000 to 200,000. When the molecular weight cut off of the first ultrafiltration membrane exceeds 200,000, the amount of the enzyme component recovered as a retentate decreases, which is thus not preferred. When the molecular weight cut off is below 100,000, the amount of enzyme components recovered by the ultrafiltration membrane excessively increase, which is thus not preferred. It is to be noted that a preferred molecular weight cut off of the first ultrafiltration membrane is 100,000 to 150,000.

And, the filtrate of step (1) is subjected to filtration with an ultrafiltration membrane with a molecular weight cut off of 5,000 to 50,000 in step (2); and enzyme components of cellulase derived from filamentous fungi that have not been fully recovered in step (1) are recovered. With the molecular weight cut off of the second ultrafiltration membrane being less than 5,000, the flux of the membrane decreases and, in addition, the amount and activity of enzyme recovered do not greatly change, which are thus not preferred. With the molecular weight cut off exceeding 50,000, the cellulase component derived from filamentous fungi contained in the filtrate of step (1) comes to be filtrated into the filtrate side and thereby the amount and activity of enzyme recovered decreases, which is thus not preferred. It is to be noted that a preferred molecular weight cut off of the second ultrafiltration membrane is 10,000 to 30,000.

The separation property of an ultrafiltration membrane (polymer membrane) is determined by the fine pore diameter of a dense layer called a function layer. As materials of the function layer of the ultrafiltration membrane used in step (1) and step (2), materials such as polyether sulfone (PES), polysulfone (PS), polyacrylonitrile (PAN), polyvinylidene difluoride (PVDF), regenerated cellulose, cellulose, cellulose ester, sulfonated polysulfone, sulfonated polyether sulfone, polyolefin, polyvinyl alcohol, polymethylmethacrylate, or polyethylene tetrafluoride can be used. Because regenerated cellulose, cellulose, and cellulose ester go through degradation by cellulase derived from *Trichoderma*, it is preferred to use an ultrafiltration membrane in which the material of the function layer is a synthetic polymer compound such as PES or PVDF.

With regard to a pH condition at the time of filtration through an ultrafiltration membrane, it is preferred in step (I) to adjust the pH of an aqueous solution of cellulase derived from filamentous fungi to pH 2.6 to 5.4 or pH 8.6 to 9.4. It is to be noted that, if the pH of the aqueous solution of cellulase derived from filamentous fungi already is a pH 2.6 to 5.4 or a pH 8.6 to 9.4, the pH thereof is considered to have adjusted to such a range. As for an effect of adjusting the pH in step (I) and then filtering through an ultrafiltration membrane, our methods have an effect by which the amount of enzyme components contained in a concentrated enzyme liquid that can be recovered as a retentate can increase.

It is to be noted that permeability of an enzyme or protein through an ultrafiltration membrane is known to change by a pH condition. This is said to be caused by the fact that the surface charge state of an enzyme or protein dissolved in an aqueous solution and thereby the apparent molecular weight thereof in the aqueous solution changes. However, it has been known that such a condition and extent of changing the apparent molecular weight are altered by various factors including a characteristic amino acid sequence and steric structure specific to each of the enzyme components and, in addition, interaction acting among respective enzymes dissolved in the aqueous solution. In the case of cellulase derived from filamentous fungi, changes in the apparent molecular weight of each enzyme component in each pH condition or association states of an individual enzyme component in the aqueous solution in which plural kinds of each enzyme component of cellulase derived from filamentous fungi are dissolved have not been clarified. Therefore, as a matter of course, changes in the permeability of each enzyme component of cellulase derived from filamentous fungi through the ultrafiltration membrane by changes in pH have not been clarified as well.

A temperature condition at the time of filtration through an ultrafiltration membrane in step (1) and step (2) is not in particular restricted as long as it is a temperature range in which enzymes are not inactivated or do not aggregate and the temperature is preferably 15 to 35° C. In particular, when the temperature exceeds 35° C., components having an enzyme activity of either xylanase or endoglucanase may in some cases aggregate, which components are enzyme components with a molecular weight of less than 40 kDa which are a part of the enzyme components of filamentous fungi cellulase.

A filtration rate by an ultrafiltration membrane of step (1) is not in particular restricted as long as it is in a range in which enzymes are blocked in the feed side and the filtration rate is preferably 0.5 to 8 m/day. With the filtration rate being less than 0.5 m/day, such a rate comes to be a factor for lowering the blocking rate of cellulase derived from filamentous fungi. On the other hand, with the filtration rate exceeding 8 m/day, such a rate may cause a marked increase in transmembrane pressure difference of the ultrafiltration membrane and abrupt fouling of the membrane.

Meanwhile, because the ultrafiltration membrane used in step (2) corresponds to the molecular weight of cellulase derived from filamentous fungi, the filtration rate less affects the blocking rate of cellulase derived from filamentous fungi and the filtration rate may be determined with consideration for the fouling of the membrane. And, the filtration rate is preferably 0.1 to 4 m/day.

It is to be noted that the filtration rate (m/day) is calculated by Formula (1), wherein the aqueous solution of cellulase derived from filamentous fungi to be filtered is subjected to filtration through the ultrafiltration membrane having a certain specific membrane area (m$^2$); and the resulting flux (m$^3$/h) is measured:

$$\text{Filtration rate (m/day)} = \text{Flux (m}^3\text{/h)} \times 24 \div \text{Membrane area (m}^2\text{)} \quad (1).$$

In step (1) and step (2), the concentration of a concentrated enzyme liquid that is obtained as a retentate of an ultrafiltration membrane is preferably 1 to 100 g/L. With the concentration exceeding 100 g/L, the viscosity of membrane-separated and concentrated enzyme liquid in the feed side increases, which may cause an abrupt drop in the filtration rate. On the other hand, with the concentration being less than 1 g/L, the solution is too dilute as the membrane-separated and concentrated enzyme liquid and thus such a concentration cannot be said to be a sufficient concentration for a reason of the use of the concentrated enzyme liquid.

As for the ultrafiltration membrane used in step (1) and step 2, one in an appropriate form such as flat membrane type, spiral type, tubular type, or hollow fiber type can be used.

In particular, because there is a possibility that an aqueous solution of cellulase derived from filamentous fungi used in step (1) contains solids or the like, a separation membrane with a strong resistance to membrane fouling is preferred. That is, an external pressure type hollow fiber ultrafiltration membrane is preferred. A hollow fiber membrane refers to a separation membrane having a hollow cavity inside of it and has function layers inside or outside of the hollow cavity. In particular, preferred is an external pressure type hollow fiber membrane capable of permeating filtration feed water from the outside of the hollow fiber membrane and obtaining a filtrate in the inside of the hollow fiber membrane. The external pressure type hollow fiber membrane has characteristics of having more strong resistance to membrane fouling by solids and, in addition, being easier to wash than an inner pressure type one.

Meanwhile, the ultrafiltration membrane that is used in step (2) may take on any form. In particular, a spiral type having a high membrane area per unit volume is preferred. Because the filtrate obtained in step (1) is used in step (2), our methods improve the filtration rate in step (2) and enable prevention of membrane fouling as well.

Concrete examples thereof include G-5 type, G-10 type, G-20 type, G-50 type, PW type, and HWS UF type, all of which are manufactured by DESAL; HFM-180, HFM-183, HFM-251, HFM-300, HFM-116, HFM-183, HFM-300, HFK-131, HFK-328, MPT-U20, MPS-U20P, and MPS-U20S, all of which are manufactured by KOCH; SPE1, SPE3, SPE5, SPE10, SPE30, SPV5, SPV50, and SOW30, all of which are manufactured by Synder; "Microza" (registered trademark) UF series manufactured by Asahi Kasei Corporation; and NTR7410 and NTR7450, both of which are manufactured by Nitto Denko Corporation.

The ultrafiltration in step (1) and step (2) may be either dead-end filtration (normal flow filtration) or cross flow filtration (tangential flow filtration). The dead-end filtration (normal flow filtration) is a method of applying pressure vertically against the membrane surface of ultrafiltration membrane to carry out filtration from the feed side to the filtrate side. On the other hand, the cross flow filtration (tangential flow filtration) is a method of carrying out filtration while removing a sedimentary layer formed on the ultrafiltration membrane surface by generating flow parallel to the membrane surface, which is a filtration direction, (cross flow or tangential flow) by a pump, air bubbles, or the like. By this cross flow (or tangential flow), membrane fouling of the ultrafiltration membrane can be prevented. In particular, when an external pressure type hollow fiber is used in step (1), the dead-end filtration is preferred. Further, when a spiral type or flat membrane type is used in step (1) and step (2), the cross flow filtration is preferred.

When the ultrafiltration membrane used in step (1) is an external pressure type hollow fiber ultrafiltration membrane, it is preferred to carry out a backwash operation in which a filtrate is intermittently passed through from the filtrate side to the feed side. By this backwash operation, deposited materials which are deposited on the membrane of the ultrafiltration membrane such as solids or enzymes, can be detached. That is, by this operation, clogging at the time of filtration by the ultrafiltration membrane can be prevented and the filtration treatment can be stably carried out for a long period of time. This operation may be carried out at the time of filtration by the ultrafiltration membrane, at the end of filtration, or the like. The timing for carrying out this operation includes cases where filtration differential pressure of the ultrafiltration membrane increases or cases where the operation is carried out at regular intervals regardless of the differential pressure. The latter is more preferred.

With regard to the concentrated enzyme liquid obtained as a retentate of the ultrafiltration membrane in step (1) or step (2), it is preferred to recover the concentrated enzyme liquid by generating cross flow by aeration and/or solution circulation in a range of a membrane surface linear velocity of 1 to 200 cm/sec. Further, on this occasion, the concentrated enzyme liquid may also be obtained while the above-described backwash operation is continuously or intermittently carried out to generate the above-described cross flow.

The obtained cellulase can be used, by being taken advantage of its own catalytic activity, in food product application, detergents, cleaning agents, environmental cleanup agents, fertilizer application, feed application, cosmetics application, pharmaceutical application, or the like.

The obtained cellulase can be widely used in hydrolysis of biomass containing cellulose. The biomass containing cellulose refers to one that contains at least cellulose or hemicellulose. Concrete examples include bagasse, corn stover, corncob, switchgrass, paddy straw, straw, tree, lumber, waste building materials, newspaper, used paper, and pulp. These biomasses containing cellulose contain impure substances such as polymer aromatic compound lignin or hemicellulose. Biomasses containing cellulose in which lignin or hemicellulose has been partially degraded by using acid, alkali, pressurized hot water, or the like as pretreatment may be used as cellulose. Hydrolysis conditions may be set to optimal reaction conditions for cellulase derived from filamentous fungi. Preferred are a treatment temperature of 40 to 60° C., a treatment pH of 3 to 7, and a concentration of the solid content of biomass containing cellulose of 0.1 to 30%. By setting to the above optimal reaction condition range, biomass hydrolysis efficiency can be brought out at a maximum. The hydrolysis treatment may be carried out by a batch method or may be carried out by a continuous method. Because a hydrolysate obtained by such an enzyme treatment contains monosaccharide components such as glucose or xylose, it can be used as fermentation raw sugar such as ethanol or lactic acid.

When the obtained cellulase is used, an enzyme component having another function such as oxidase, reductase, hydrolase, transferase, or isomerase may be added to be used as an enzyme agent. In particular, such an enzyme component having another function is not limited to filamentous fungi and enzyme components derived from any organisms or enzyme components produced by gene recombination may be added and used.

Figure 4:
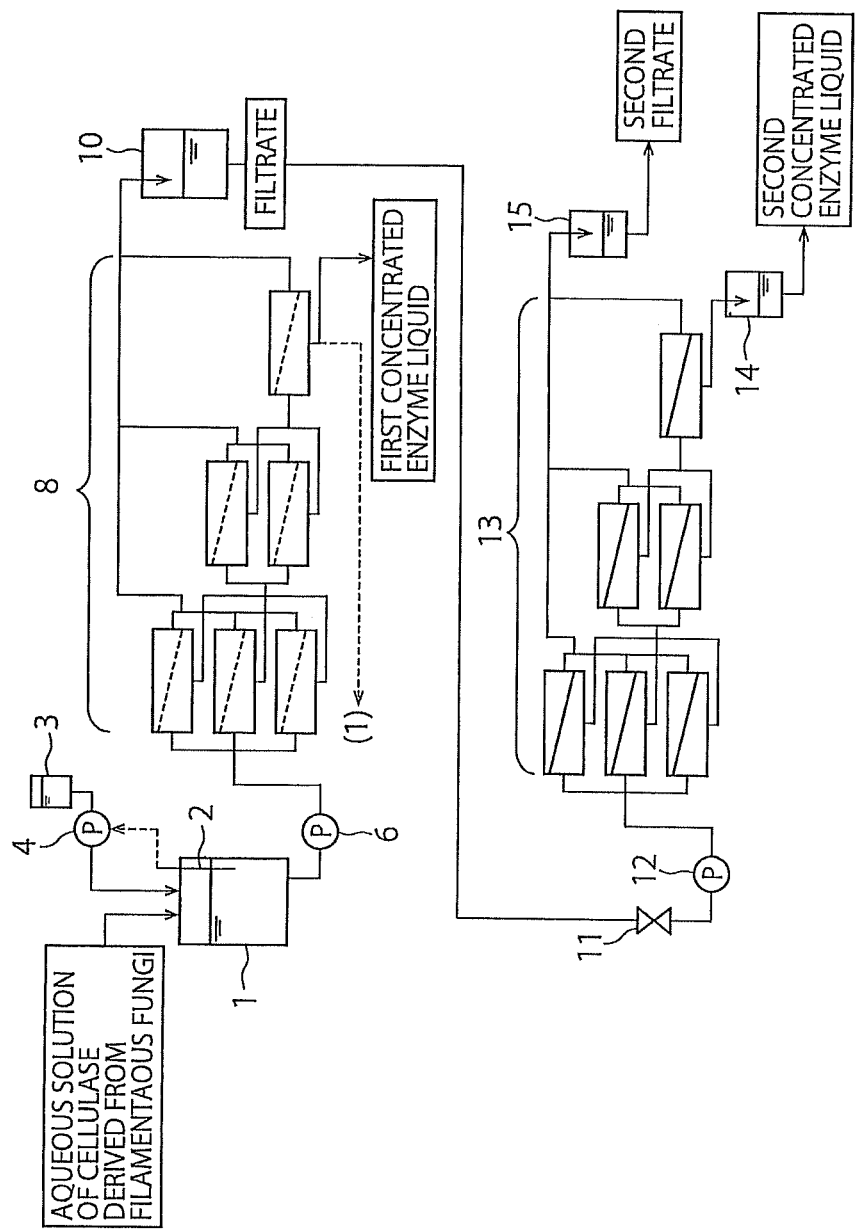
FIG. 4 is a cross section view showing one example of a device for carrying out our method of producing cellulase.
Figure 5:
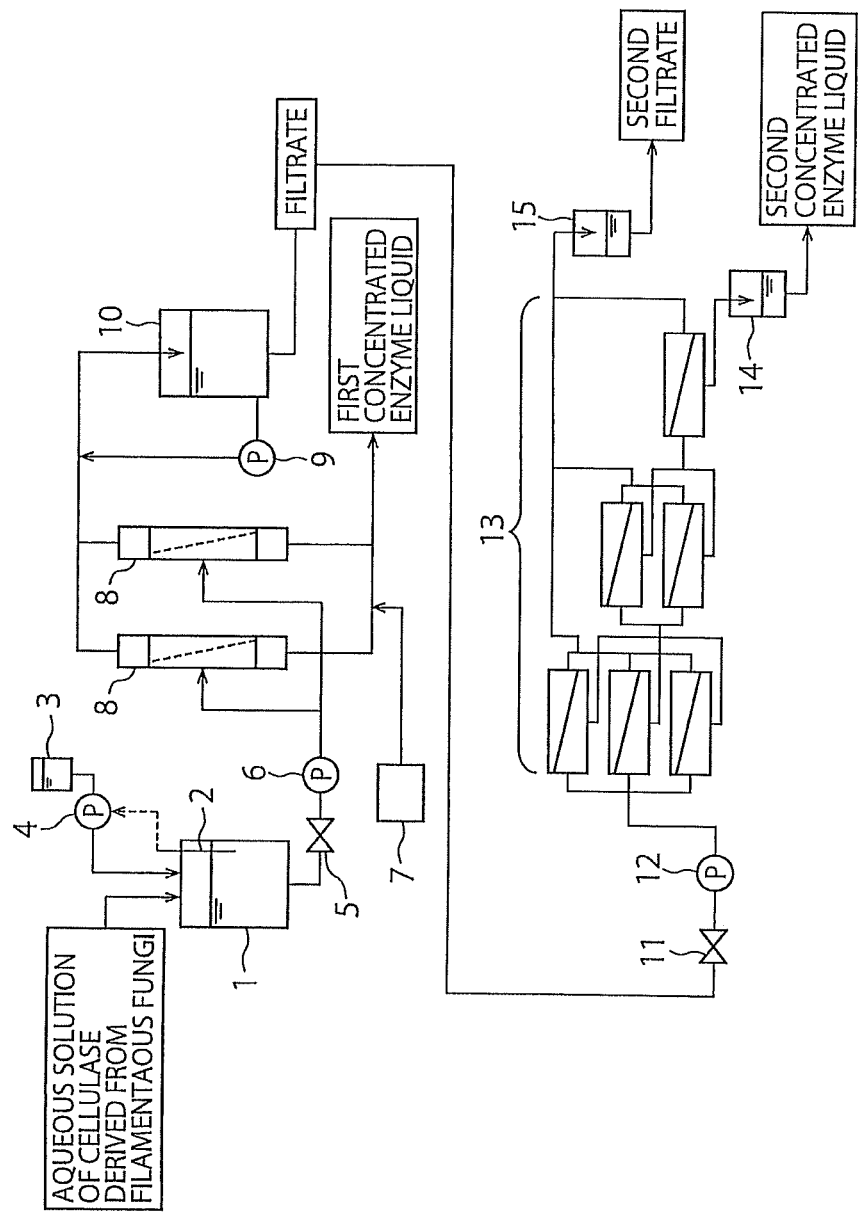
FIG. 5 is a cross section view showing another example of a device for carrying out our method of producing cellulase.

Our devices will be described using FIGS. 4 and 5 as examples thereof. FIGS. 4 and 5 are cross sectional views depicting one example of the device of carrying out our methods.

The device of FIG. 4 is a spiral element type device that utilizes an ultrafiltration membrane with a molecular weight cut off of 100,000 to 200,000. An aqueous solution of cellulase derived from filamentous fungi is held in the tank for an aqueous solution of cellulase 1. In this tank 1, adjustment of pH is carried out and thus the pH sensor 2 is installed in the tank. A detected pH signal is transferred to the pH adjustment pump 3. The pH adjustment pump 3 is connected to the pH adjuster tank 4 which contains an acid or alkali; and a pH adjuster is sent to the tank for an aqueous solution of cellulase 1. The tank for an aqueous solution of cellulase 1 is connected to the ultrafiltration membrane 8 with a molecular weight cut off of 100,000 to 200,000 via the ultrafiltration pump 6.

In the device of FIG. 4, the ultrafiltration membrane 8 with a molecular weight cut off of 100,000 to 200,000 is connected in a tree structure. Yet, there are no particular limitations. Further, the filtrate of the ultrafiltration membrane 8 with a molecular weight cut off of 100,000 to 200,000 is connected to the holding tank for filtrate 10. The retentate of the ultrafiltration membrane 8 with a molecular weight cut off of 100,000 to 200,000 is recovered as the first concentrated enzyme liquid. The concentrated enzyme liquid which is the retentate may be recovered as is as the first concentrated enzyme liquid as long as necessary and sufficient separation and concentration can be attained; and the concentrated enzyme liquid may be connected to the tank for an aqueous solution of cellulase 1 for circulation to obtain a more sufficient concentration rate.

With regard to the filtrate of the ultrafiltration membrane with a molecular weight cut off of 100,000 to 200,000, separation and concentration are further carried out with the second ultrafiltration membrane with an average molecular weight cut off 5,000 to 50,000. The holding tank for filtrate 10 connects to the ultrafiltration membrane 13 with a molecular weight cut off of 5,000 to 50,000 via the valve 11 and the ultrafiltration pump 12. As shown in FIG. 4, the ultrafiltration membrane 13 with a molecular weight cut off of 5,000 to 50,000 may connect in a tree structure. The retentate of the ultrafiltration membrane 13 with a molecular weight cut off of 5,000 to 50,000 is recovered as a concentrated enzyme liquid. The concentrated enzyme liquid is recovered in the second holding tank for concentrated enzyme liquid 14 and the filtrate is recovered in the second holding tank for filtrate 15.

The device of FIG. 5 is an example in which an external pressure type hollow fiber ultrafiltration membrane is used as the ultrafiltration membrane 8 with a molecular weight cut off of 100,000 to 200,000. When the external pressure type hollow fiber ultrafiltration membrane is used, the device comprises the compressor 7 which generates air bubbles to wash the hollow fiber membrane surface and the backwash pump 9 to carry out backwash of the membrane by using the filtrate of the ultrafiltration membrane 8 with a molecular weight cut off of 100,000 to 200,000. The rest is same as described in the device of FIG. 4.

EXAMPLES

By way of example, our methods will now be concretely described below. This disclosure is, however, not limited thereto.

Reference Example 1

Method of Preparing Culture Solution of *Trichoderma*

A culture liquid of *Trichoderma* was prepared by the following method. Preculture Corn steep liquor 5% (w/vol), glucose 2% (w/vol), ammonium tartrate 0.37% (w/vol), ammonium sulfate 0.14 (w/vol), potassium dihydrogen phosphate 0.2% (w/vol), calcium chloride dihydrate 0.03% (w/vol), magnesium sulfate heptahydrate 0.03% (w/vol), zinc chloride 0.02% (w/vol), iron (III) chloride hexahydrate 0.01% (w/vol), copper (II) sulfate pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol) were added to distilled water; and 100 mL of the resultant was filled into a 500 mL Erlenmeyer flask with baffles and subjected to autoclave sterilization at a temperature of 121° C. for 15 minutes. After allowed to cool, the resultant was added with each of PE-M and Tween80 at 0.01% (w/vol), which PE-M and Tween80 had been independently subjected to autoclave sterilization at a temperature of 121° C. for 15 minutes. *Trichoderma reesei* ATCC66589 was seeded to this preculture medium to be $1 \times 10^5$ cells/mL and cultured at a temperature of 28° C. for 72 hours with shaking at 180 rpm (shaking device: BIO-SHAKER BR-40LF manufactured by TAITEC), thereby obtaining preculture.
Main Culture Corn steep liquor 5% (w/vol), glucose 2% (w/vol), cellulose (Avicel) 10% (w/vol), ammonium tartrate 0.37% (w/vol), ammonium sulfate 0.14% (w/vol), potassium dihydrogen phosphate 0.2% (w/vol), calcium chloride dihydrate 0.03% (w/vol), magnesium sulfate heptahydrate 0.03%

(w/vol), zinc chloride 0.02% (w/vol), iron (III) chloride hexahydrate 0.01% (w/vol), copper (II) sulfate pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol) were added to distilled water; and 2.5 L of the resultant was filled into a 5 L-stirring jar (manufactured by ABLE, DPC-2A) vessel and subjected to autoclave sterilization at a temperature of 121° C. for 15 minutes. After allowed to cool, the resultant was added with each of PE-M and Tween80 at 0.1%, which PE-M and Tween80 had been separately subjected to autoclave sterilization at a temperature of 121° C. for 15 minutes; and 250 mL of *Trichoderma reesei* ATCC66589 that had pre-cultured in advance in liquid medium by the above-mentioned method was inoculated. Thereafter, the culture was carried out with shaking at a temperature of 28° C. for 87 hours at 300 rpm in a condition of an aeration volume of 1 vvm; and after centrifugation, the supernatant was subjected to membrane filtration ("STERICUP"-GV manufactured by Millipore, material: PVDF). This culture liquid adjusted in the above-described condition was used in the following examples as an aqueous solution of cellulase derived from *Trichoderma*.

Reference Example 2

Measurement of Sugar Concentration

The concentration of glucose and xylose that were contained in a sugar liquid was quantified in HPLC conditions described below by comparing to a standard sample:
Column: Luna $NH_2$ (manufactured by Phenomenex)
Mobile phase: Milli-Q:acetonitrile=25:75 (flow rate 0.6 mL/min)
Reaction liquid: None
Detection method: RI (differential refractive index)
Temperature: 30° C.

Reference Example 3

Method of Measuring Cellulase Activity

The cellulase activity was divided into three kinds of degrading activities: (1) Avicel degrading activity, (2) cellobiose degrading activity, and (3) xylan degrading activity; and the activity was measured and evaluated via the following procedure.
(1) Avicel Degrading Activity
To an enzyme liquid (prepared in predetermined conditions), Avicel (manufactured by Merck) 1 g/L and sodium acetate buffer (pH 5.0) were added at 100 mM. The resulting mixture was, while rotated and mixed, allowed to react at a temperature of 50° C. for 24 hours. After the reaction, a tube was centrifuged and the glucose concentration of the supernatant component was measured. The glucose concentration was measured according to the method described in Reference Example 2. The concentration of glucose produced (g/L) was used as is as the activity level of the Avicel degrading activity.
(2) Cellobiose Degrading Activity
To an enzyme liquid, cellobiose (Wako Pure Chemical Industries, Ltd.) 500 mg/L and sodium acetate buffer (pH 5.0) were added at 100 mM. The resulting mixture was, while rotated and mixed, allowed to react at a temperature of 50° C. for 0.5 hours. After the reaction, a tube was centrifuged and the glucose concentration of the supernatant component was measured. The glucose concentration was measured according to the method described in Reference Example 2. The concentration of glucose produced (g/L) was used as is as the activity level of the cellobiose degrading activity.
(3) Xylan Degrading Activity
To an enzyme liquid, xylan (Birch wood xylan, Wako Pure Chemical Industries, Ltd.) 10 g/L and sodium acetate buffer (pH 5.0) were added at 100 mM. The resulting mixture was, while rotated and mixed, allowed to react at a temperature of 50° C. for four hours. After the reaction, a tube was centrifuged and the xylose concentration of the supernatant component was measured. The xylose concentration was measured according to the method described in Reference Example 2. The concentration of xylose produced (g/L) was used as is as the activity level of the xylose degrading activity.

Reference Example 4

Measurement of Protein Concentration

Measurement of protein concentration was carried out using Pierce BCA Protein Assay Kit according to the Kit protocol. A standard curve of protein concentration was prepared by measuring, in the same manner, ones obtained by subjecting Albumin standard (2 mg/mL) to serial dilution; and quantification was carried out by target samples of the standard curve and colorimetry.

Reference Example 5

Membrane Separation and Concentration of Aqueous Solution of Cellulase Derived from *Trichoderma* by Ultrafiltration Membrane with Molecular Weight Cut Off of 100,000

The cellulase derived from *Trichoderma* prepared of the above Reference Example 1 was diluted to be 3.5 g/L. For this, dilute hydrochloric acid or dilute sodium hydroxide was used to prepare an aqueous solution with pH 2, pH 3, pH 4, pH 5, pH 6, pH 7, pH 8, pH 9, pH 10, pH 11, and pH 12 (pH 2 to 12). After adjustment of pH, the protein concentration was measured again and found to be approximately 3.5 g/L. Thus, the protein concentration of these aqueous solutions of cellulase whose pH had been adjusted was considered to be presumably 3.5 g/L and the following evaluation was carried out.

The above-mentioned aqueous solution of cellulase derived from *Trichoderma* whose pH had been adjusted (pH 2 to 12) 20 mL was each concentrated using an ultrafiltration membrane with a molecular weight cut off of 100,000 ("VIVASPIN" 20 manufactured by Sartorius, 100,000 MWCO, PES, effective membrane area 6 $cm^2$) via dead-end filtration until the liquid volume of retentate reached 0.5 mL (temperature 25° C., centrifugal force 6000 g). To measure the amount of proteins of the concentrated liquid and the cellulase activity thereof, the concentrated liquid was recovered and, with the mass thereof being measured, filled with RO water until reaching its initial mass of 20 g (20 mL). This was used, as a retentate, in the following analysis. Further, as for a filtrate, a filtrate of the ultrafiltration membrane was not subjected to particular treatment such as dilution and was used as is as the filtrate in the following analysis.

Figure 2:
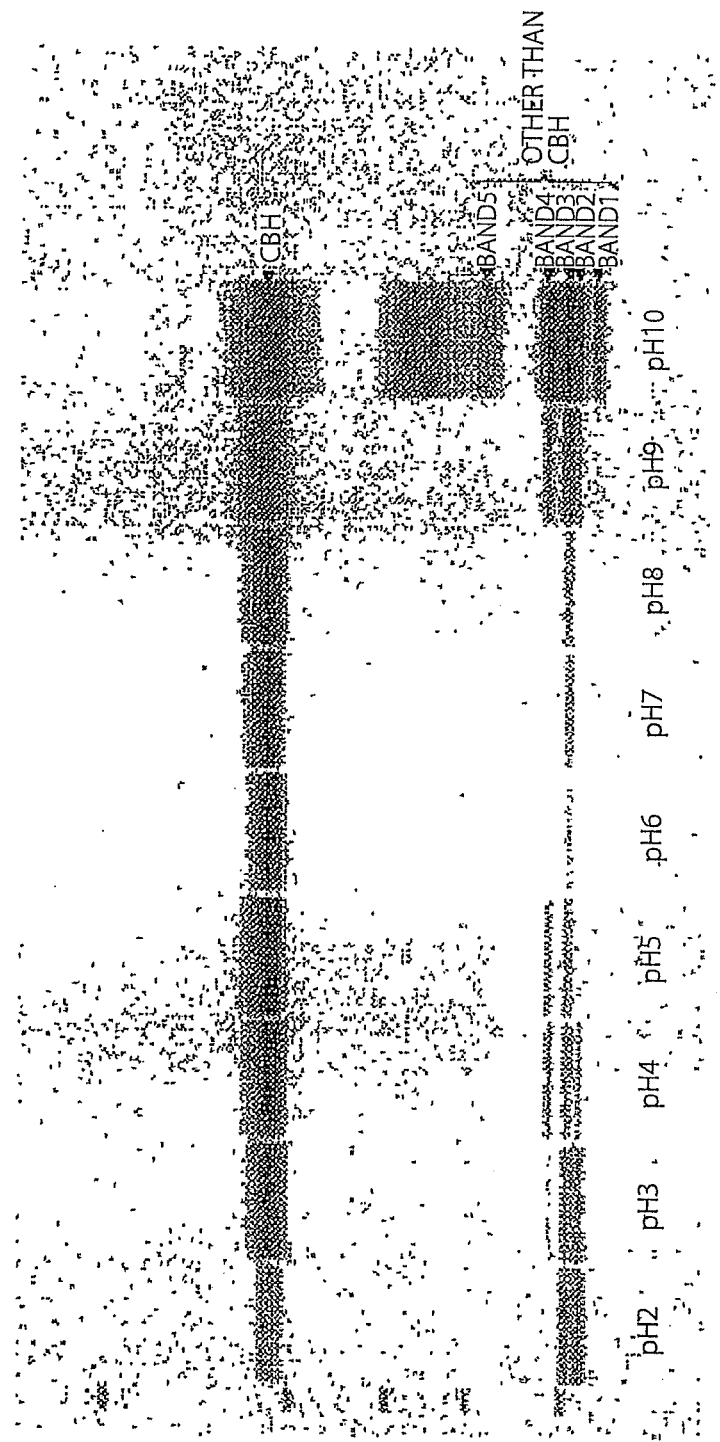
FIG. 2 is a drawing showing the result of analysis of a concentrated enzyme liquid by a bioanalyzer (Agilent, Protein 230 kit), which concentrated enzyme liquid has been obtained by adjusting the pH of cellulase derived from *Trichoderma* to various pH and subjecting the resultant to filtration through the first ultrafiltration membrane with a molecular weight cut off of 100,000 to 200,000 to separate as a retentate.

Measurement of the protein concentration of the retentate and filtrate was carried out by the method described in the above Reference Example 4. Further, for the above-described retentate and filtrate, electrophoresis was carried out using a bioanalyzer (Agilent, Protein 230 kit). The obtained result of electrophoresis is shown in FIG. 2. In FIG. 2, a band ascribed to cellobiohydrolase of cellulase derived from *Trichoderma* can be confirmed at any pH of pH 2 to 10 and we found that there was difference in the intensity of each band depending on the pH of an aqueous solution of *Trichoderma* cellulase. In particular, we found that the band intensity of cellobiohydrolase (CBH) is high at pH 3, pH 4, and pH 5 (FIG. 2) and the band intensity of cellobiohydrolase tended to be low in the case of being above pH 6 or in the case of being pH 2. Further, we confirmed that this result was totally consistent with a tendency in cellobiohydrolase concentration calculated by a bioanalyzer. The result is shown in Table 1.

TABLE 1

|  | pH 2 | pH 3 | pH 4 | pH 5 | pH 6 | pH 7 | pH 8 | pH 9 | pH 10 |
|---|---|---|---|---|---|---|---|---|---|
| CBH concentration (µg/Ml) | 508 | 1300 | 1273 | 1615 | 1142 | 978 | 847 | 870 | 545 |

Next, measurement of each cellulase activity of the retentate was carried out according to the above Reference Example 3. The result is shown in Table 2.

TABLE 2

|  | pH 2 | pH 3 | pH 4 | pH 5 | pH 6 | pH 7 |
|---|---|---|---|---|---|---|
| Recovery rate of protein | 78% | 57% | 59% | 47% | 43% | 40% |
| Avicel degrading activity | 0 | 0.25 | 0.24 | 0.2 | 0 | 0 |
| Xylan degrading activity | 1.4 | 1.6 | 1.5 | 1.1 | 0.9 | 0.9 |
| Cellobiose degrading activity | 0 | 0.3 | 0.3 | 0.3 | 0.2 | 0.1 |

|  | pH 8 | pH 9 | pH 10 | pH 11 | pH 12 |
|---|---|---|---|---|---|
| Recovery rate of protein | 27% | 71% | 73% | 75% | 73% |
| Avicel degrading activity | 0 | 0.21 | 0 | 0 | 0 |
| Xylan degrading activity | 0.7 | 1.1 | 0.5 | 0 | 0 |
| Cellobiose degrading activity | 0 | 0.4 | 0 | 0 | 0 |

The cellulase degrading activity of the retentate, in particular Avicel degrading activity at each pH was compared. We found that the activity was higher in a condition of pH 3, pH 4, pH 5, and pH 9 than other pH. That was thought to be because the activity correlated with the amount of cellobiohydrolase recovered in Table 1 at pH 3, pH 4, and pH 5; and the amount of cellobiohydrolase recovered increased among the cellulase components derived from *Trichoderma* at pH 3, pH 4, and pH 5. Further, in contrast, it was found that the Avicel degrading activity increased at a condition of pH 9. It was found that this result did not correlate with the result of electrophoresis in FIG. 2 or the amount of cellobiohydrolase recovered in Table 1. To check the reason, analysis was carried out for band 1 to band 5 other than cellobiohydrolase in FIG. 2 using a bioanalyzer. The molecular weight of each of band 1 to band 5 was: band 1: 23.5 kDa, band 2: 26.1 kDa, band 3: 27.6 kDa, band 4: 30.8 kDa, and band 5: 42.5 kDa, respectively. Further, similarly to CBH, the concentration of each cellulase component of bands 1 to 5 was calculated by a bioanalyzer. The result is shown in Table 3.

TABLE 3

|  | pH 2 | pH 3 | pH 4 | pH 5 | pH 6 | pH 7 | pH 8 | pH 9 | pH 10 |
|---|---|---|---|---|---|---|---|---|---|
| Band 1 (µg/ml) | 95 | 71 | 51 | 44 | 27 | 21 | 22 | 84 | 70 |
| Band 2 (µg/ml) | 268 | 242 | 138 | 105 | 55 | 27 | 24 | 103 | 84 |
| Band 3 (µg/ml) | 268 | 242 | 138 | 105 | 55 | 27 | 24 | 103 | 84 |
| Band 4 (µg/ml) | 25 | 117 | 152 | 131 | 68 | 52 | 45 | *214 | 296 |
| Band 5 (µg/ml) | 58 | 54 | 63 | 59 | 32 | 21 | 24 | *126 | 129 |

As a result of the analysis, we found that, as for bands 1 to 5 of cellulase components, the amount recovered as a retentate increased at pH 3, pH 4, pH 5, and pH 9. It is to be noted that band 4 and band 5 of cellulase components were in particular found to be present as bands with increased amount recovered at pH 9 or higher (Table 3, *: asterisk). With regard to these two kinds of enzyme components, it was thought that the Avicel degrading activity of the retentate increased because a large amount thereof was specifically recovered as the retentate at pH 9. Identification of band 4 and band 5 has not been completed. Nevertheless, from the molecular weight of cellulase derived from *Trichoderma* component written in a known database, it was presumed that they are endoglucanase or xylanase.

Further, while the recovery rate of the protein was high at a condition of pH 10 or higher, the recovery rate of the enzyme activity significantly decreased. This was thought to be because even though the protein of cellulase component derived from *Trichoderma* could be recovered at pH 10 or higher, the enzyme activity thereof was inactivated. It was thought that the recovery rate of the enzyme activity significantly decreased also at pH 2 due to the same reason as at pH 10 or higher.

That is, we found that the cellulase activity recovered as the retentate increased or decreased by adjusting the pH of the aqueous solution of cellulase derived from *Trichoderma* in Reference Example 5. Further, in particular, we confirmed that because the cellulase degrading activity recovered became maximum at pH 3, pH 4, pH 5, and pH 9, a retentate having a high cellulase degrading activity could be recovered by adjusting the pH of the aqueous solution of cellulase derived from *Trichoderma* to a range of pH 2.6 to 5.4 or pH 8.6 to 9.4 and then by subjecting to filtration through the ultrafiltration membrane with a molecular weight cut off of 100,000.

Comparative Example 1

Concentration of Cellulase Derived from *Trichoderma* by Ultrafiltration Membrane with Molecular Weight Cut Off of 10,000 (pH 3 and pH 9)

20 mL of the aqueous solution of cellulase derived from *Trichoderma* (pH 3, pH 9) of Reference Example 5 was concentrated using an ultrafiltration membrane with a molecular weight cut off of 10,000 ("VIVASPIN" 20 manufactured by Sartorius, 10,000 MWCO, PES, effective membrane area 6 cm$^2$) via dead-end filtration until the liquid volume of retentate reached 1 mL (temperature 25° C., centrifugal force 6000 g). The concentrated liquid was recovered and, with the mass thereof being measured, filled with RO water until reaching its initial mass of 20 g. This was used as a retentate and the cellulase degrading activity thereof was measured according to the above Reference Example 3. With regard to the aqueous solution of cellulase derived from *Trichoderma* before ultrafiltration, the cellulase degrading activity of the retentate was evaluated with an activity value obtained by the measurement according to Reference Example 3 as 100%. The obtained result is shown in Table 5.

Example 1

Membrane Separation and Concentration of Aqueous Solution of Cellulase Derived from *Trichoderma* by Ultrafiltration Membranes with Molecular Weight Cut Off of 100,000 and 10,000 (pH 3 and 9)

As shown in Reference Example 5, we found that a part of the cellulase components could be recovered in the feed side by subjecting an aqueous solution of cellulase derived from *Trichoderma* to filtration through an ultrafiltration membrane with a molecular weight cut off of 100,000. However, a concurrent problem was, on another front, that a part of the enzyme components were lost as a filtrate of the ultrafiltration membrane. In view of this, we examined whether the second concentrated enzyme liquid was further obtained as a retentate by further subjecting the filtrate to filtration using an ultrafiltration membrane with a molecular weight cut off of 10,000 after separating the aqueous solution of cellulase derived from *Trichoderma* by the ultrafiltration membrane with a molecular weight cut off of 100,000 and recovering the retentate (the first concentrated enzyme liquid). To be specific, the examination was carried out by the following procedure.

The ultrafiltration was carried out using the aqueous solution of cellulase derived from *Trichoderma* in Reference Example 5 (pH 3 and pH 9). Filtration by the ultrafiltration membrane with a molecular weight cut off of 100,000 was carried out according to Comparative Example 1; and the retentate (the first concentrated enzyme liquid) 0.5 mL and the filtrate 19.5 mL were recovered.

The filtrate 19.5 mL was further concentrated using the second ultrafiltration membrane with a molecular weight cut off of 10,000 ("VIVASPIN" 20 manufactured by Sartorius, 10,000 MWCO, PES, effective membrane area 6 cm$^2$) via dead-end filtration until the liquid volume of the retentate reached 0.5 mL (temperature 25° C., centrifugal force 6000 g). Eventually, the first concentrated enzyme liquid 0.5 mL and the second concentrated enzyme liquid 0.5 mL were mixed, thereby obtaining a recovered enzyme liquid 1 mL.

Next, the recovered enzyme liquid was, with the mass thereof being measured, filled with RO water until reaching its initial mass of 20 g; and the cellulase degrading activity of the resulting liquid was measured according to the above Reference Example 3. Further, also with regard to the aqueous solution of cellulase derived from *Trichoderma* before ultrafiltration, the cellulase degrading activity of the retentate was evaluated with an activity value obtained by measuring the cellulase degrading activity according to Reference Example 3 as 100%. The obtained result is shown in Table 4.

TABLE 4

|  | pH 3.0 | | pH 9.0 | |
| --- | --- | --- | --- | --- |
|  | Comparative Example 1 | Example 1 | Comparative Example 1 | Example 1 |
| Recovery rate of protein | 82% | 86% | 78% | 84% |
| Recovery rate of Avicel degrading activity | 81% | 98% | 82% | 98% |
| Recovery rate of xylan degrading activity | 96% | 97% | 92% | 97% |
| Recovery rate of cellobiose degrading activity | 98% | 102% | 80% | 93% |

When the concentrated enzyme liquid obtained using only the ultrafiltration membrane with a molecular weight cut off of 10,000 in Comparative Example 1 was compared to the recovered enzyme liquid obtained by mixing the first concentrated enzyme liquid obtained using the ultrafiltration membrane with a molecular weight cut off of 100,000 with the second concentrated enzyme liquid obtained using the ultrafiltration membrane with a molecular weight cut off of 10,000 in Example 1, we found that the recovery rate of the protein increased more in Example 1 than in Comparative Example 1. In addition, we found that, in Example 1, the recovery rate of the Avicel degrading activity significantly increased in particular.

That is, from the result of Example 1, we found that the enzyme amount of the recovered cellulase derived from *Trichoderma* and the activity thereof could increase by carrying out the step of obtaining the first concentrated enzyme liquid using an ultrafiltration membrane with a molecular weight cut off of 100,000 to 200,000, and then the step of obtaining the second concentrated enzyme liquid by subjecting the filtrate to filtration through a the second ultrafiltration membrane of 5,000 to 50,000.

Example 2

Critical Flux of Second Ultrafiltration Membrane

The aqueous solution of cellulase derived from *Trichoderma* 1 L (pH 5) *Trichoderma* aqueous solution in Reference Example 5 was subjected to cross flow filtration through a hollow fiber ultrafiltration membrane with a molecular weight cut off of 150,000 ("TORAYFIL" HFU manufactured by Toray Industries, Inc.) to obtain a filtrate. Next, the cross flow filtration was carried out using an ultrafiltration membrane with a molecular weight cut off of 10,000 (VIVA-SCIENCE, "VIVAFLOW" 50, PES, VF05P0) with the filtration flux being changed, thereby measuring transmembrane pressure difference at each filtration flux. For comparison, also with regard to the case where a hollow fiber ultrafiltration membrane with a molecular weight cut off of 150,000 was not carried out (which was designated as Comparative Example 2), the filtration was carried out in the same manner as described above, using an ultrafiltration membrane with a molecular weight cut off of 10,000 with the filtration flux being changed, thereby measuring transmembrane pressure difference at each filtration flux. The result is shown in FIG. 3.

Figure 3:
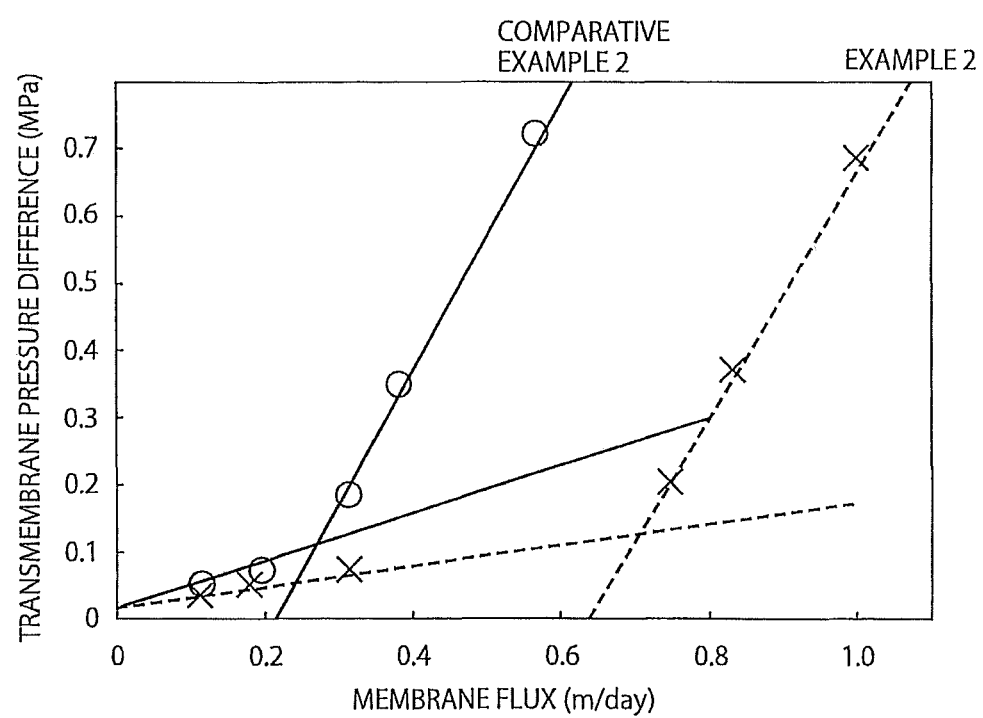
FIG. 3 is a drawing showing the critical flux of an ultrafiltration membrane at the time of obtaining the second concentrated enzyme liquid.

As shown in FIG. 3, a regression line was prepared using three points where the transmembrane pressure difference sharply increased and a point before the increase. Membrane flux (m/day) at the intersection point of two regression lines was designated as critical membrane flux. As a result, we found that the filtrate obtained by treating the aqueous solution of cellulase derived from *Trichoderma* through the hollow fiber ultrafiltration membrane with a molecular weight cut off of 150,000 exhibited a more increased value of the critical membrane flux. This is thought to be because a part of the enzyme components or other water-soluble polymer components are removed by the hollow fiber ultrafiltration membrane with a molecular weight cut off of 150,000 and the critical flux of a molecular weight cut off of 10,000 increases. Further, it is the result showing that this effect enables the flux of the second ultrafiltration membrane to be set high and time for concentration and energy used therefor can be reduced.

Comparative Example 3

Concentration of Cellulase Derived from *Trichoderma* by Ultrafiltration Membrane with Molecular Weight Cut Off of 10,000 (pH 4, pH 5, pH 6, pH 7, and pH 8)

While the evaluation in the cases of pH 3 and pH 9 was carried out in Comparative Example 1, the example was carried out at pH 4, pH 5, pH 6, pH 7, and pH 8 (pH 4 to 8) via the following procedure.

20 mL of the aqueous solution of cellulase derived from *Trichoderma* (pH 4 to 8) of Reference Example 5 was each concentrated until the liquid volume of the retentate reached 1 mL via the same procedure as described in Comparative Example 1. The concentrated liquid was recovered and, with the mass thereof being measured, filled with RO water until reaching its initial mass of 20 g; and the cellulase degrading activity was measured according to the above Reference Example 3. Also with regard to the aqueous solution of cellulase derived from *Trichoderma* before ultrafiltration, the cellulase degrading activity of the retentate was evaluated with an activity value obtained by measuring the cellulase degrading activity according to Reference Example 3 as 100%. The obtained result is shown in Table 5.

Example 3

Membrane Separation and Concentration of Aqueous Solution of Cellulase Derived from Genus *Trichoderma* by Ultrafiltration Membranes with Molecular Weight Cut Off of 100,000 and 10,000 (pH 4, pH 5, pH 6, pH 7, and pH 8)

While the evaluation in step (2) was carried out in the cases of pH 3 and pH 9 in Example 1, an evaluation on whether the effects in step (1) and step (2) were exerted was carried out at pH 4, pH 5, pH 6, pH 7, and pH 8 (pH 4 to 8) via the following procedure.

The aqueous solution of cellulase derived from *Trichoderma* of Reference Example 5 (pH 4 to 8) 20 mL was each subjected to the same procedure as described in Example 1 to recover a retentate (the first concentrated enzyme liquid) 0.5 mL and a filtrate 19.5 mL. Further, also as for the filtrate 19.5 mL, concentration was carried out until the liquid volume of the retentate reached 0.5 mL via the same procedure as described in Example 1, thereby obtaining the second concentrated enzyme liquid. Eventually, the first concentrated enzyme liquid 0.5 mL and the second concentrated enzyme liquid 0.5 mL were mixed, thereby obtaining a recovered enzyme liquid 1 mL.

Next, the recovered enzyme liquid was, with the mass thereof being measured, filled with RO water until reaching its initial mass of 20 g; and the cellulase degrading activity of the resulting liquid was measured according to the above Reference Example 3. Further, also with regard to the aqueous solution of cellulase derived from *Trichoderma* before ultrafiltration, the cellulase degrading activity of the retentate was evaluated with an activity value obtained by measuring the cellulase degrading activity according to Reference Example 3 as 100%. The obtained result is shown in Table 5.

TABLE 5

|  | pH 4.0 | | pH 5.0 | |
| --- | --- | --- | --- | --- |
|  | Comparative Example 3 | Example 3 | Comparative Example 3 | Example 3 |
| Recovery rate of protein | 80% | 85% | 78% | 84% |
| Recovery rate of Avicel degrading activity | 81% | 98% | 82% | 96% |

|  | pH 6.0 | | pH 7.0 | |
| --- | --- | --- | --- | --- |
|  | Comparative Example 3 | Example 3 | Comparative Example 3 | Example 3 |
| Recovery rate of protein | 72% | 83% | 70% | 80% |
| Recovery rate of Avicel degrading activity | 76% | 90% | 70% | 88% |

|  | pH 8.0 | |
| --- | --- | --- |
|  | Comparative Example 3 | Example 3 |
| Recovery rate of protein | 70% | 80% |
| Recovery rate of Avicel degrading activity | 70% | 88% |

When the concentrated enzyme liquid (pH 4 to 8) obtained using only the ultrafiltration membrane with a molecular weight cut off of 10,000 in Comparative Example 3 was compared to the recovered enzyme liquid obtained by mixing the first concentrated enzyme liquid obtained using the ultrafiltration membrane with a molecular weight cut off of 100,000 with the second concentrated enzyme liquid obtained using the ultrafiltration membrane with a molecular weight cut off of 10,000 in Example 3, it was found that the recovery rate of the protein increased more in Example 3 than in Comparative Example 3. In addition, it was found that, in Example 3, the recovery rate of the Avicel degrading activity significantly increased in particular.

That is, from the result of Example 3, we found that the enzyme amount of a recovered cellulase derived from *Trichoderma* ion and the activity thereof could be increased by carrying out the step of obtaining the first concentrated enzyme liquid using the ultrafiltration membrane with a molecular weight cut off of 100,000 to 200,000 at pH 4 to 8, and then the step of obtaining the second concentrated enzyme liquid by subjecting the filtrate to filtration through a the second ultrafiltration membrane of 5,000 to 50,000.

Further, when the result of Example 1 (pH 3 and pH 9) was compared with the result of Example 3 (pH 4 to 8), it was found that the recovery rate of the Avicel degrading activity of the cellulase recovered was higher in conditions of pH 3 in Example 1, pH 4 in Example 3, and pH 9 in Example 1, as compared with the result of "pH 6, pH 7, and pH 8" in Example 3. That is, it was found that the pH of the aqueous solution of filamentous fungi cellulase is preferably adjusted to pH 2.6 to 5.4 or pH 8.6 to 9.4.

Comparative Example 4

Membrane Separation and Concentration of Aqueous Solution of Cellulase Derived from Genus *Trichoderma* by Molecular Weight Cut Off of 10,000 and Molecular Weight Cut Off of 10,000 (pH 3 and pH 9)

The aqueous solution of cellulase derived from *Trichoderma* of Reference Example 5 (pH 3 and pH 9) 20 mL was each concentrated until the liquid volume of the retentate reached 0.5 mL via the same procedure as described in Comparative Example 1 to recover a retentate (the first concentrated enzyme liquid) 0.5 mL and a filtrate 19.5 mL.

Next, the filtrate 19.5 mL was further concentrated using the second ultrafiltration membrane with a molecular weight cut off of 10,000 ("VIVASPIN" 20 manufactured by Sartorius, 10,000 MWCO, PES, effective membrane area 6 cm$^2$) until the liquid volume of the retentate reached 0.5 mL via the same procedure as described in Comparative Example 1, thereby recovering the second concentrated enzyme liquid. Eventually, the first concentrated enzyme liquid 0.5 mL and the second concentrated enzyme liquid 0.5 mL were mixed, thereby obtaining a recovered enzyme liquid 1 mL.

Next, the recovered enzyme liquid was, with the mass thereof being measured, filled with RO water until reaching its initial mass of 20 g; and the cellulase degrading activity of the resulting liquid was measured according to the above Reference Example 3. Further, also with regard to the aqueous solution of cellulase derived from *Trichoderma* before ultrafiltration, the cellulase degrading activity of the retentate was evaluated with an activity value obtained by measuring the cellulase degrading activity according to Reference Example 3 as 100%. The obtained result is shown in Table 6.

TABLE 6

|  | pH 3 | pH 9 |
|---|---|---|
| Recovery rate of protein | 82% | 79% |
| Recovery rate of Avicel degrading activity | 81% | 82% |
| Recovery rate of xylan degrading activity | 96% | 92% |
| Recovery rate of cellobiose degrading activity | 98% | 81% |

As compared to the result of the concentration (in the cases of pH 3 and pH 9) of cellulase derived from *Trichoderma* by the ultrafiltration membrane with a molecular weight cut off of 10,000 in Comparative Example 1, we confirmed that the amount of proteins recovered and the amount of Avicel degrading activity recovered in Comparative Example 4 did not differ greatly.

Comparative Example 5

Concentration of Cellulase Derived from *Trichoderma* by Ultrafiltration Membrane with Molecular Weight Cut Off of 30,000 (pH 3 and pH 9)

While the ultrafiltration membrane with a molecular weight cut off of 10,000 was used in Comparative Example 1, an ultrafiltration membrane with a molecular weight cut off of 30,000 ("VIVASPIN" 20 manufactured by Sartorius, 30,000 MWCO, PES, effective membrane area 6 cm$^2$) was used in this Comparative Example 5 to carry out the example. The same procedure as in Comparative Example 1 was carried out except for the molecular weight cut off of the above-mentioned ultrafiltration membrane used. The obtained result is shown in Table 7.

Example 4

Membrane Separation and Concentration of Aqueous Solution of Cellulase Derived from *Trichoderma* (pH 3 and 9) by Ultrafiltration Membranes with Molecular Weight Cut Off of 100,000 and 30,000

While the ultrafiltration membrane with a molecular weight cut off of 10,000 was used as the second ultrafiltration membrane in Example 1, an ultrafiltration membrane with a molecular weight cut off of 30,000 ("VIVASPIN" 20 manufactured by Sartorius, 30,000 MWCO, PES, effective membrane area 6 cm$^2$) was used in this Example 4 to carry out the example. The same procedure as Example 1 was carried out except for the molecular weight cut off of the above-mentioned ultrafiltration membrane used. The obtained result is shown in Table 7.

TABLE 7

|  | pH 3.0 | | pH 9.0 | |
|---|---|---|---|---|
|  | Comparative Example 5 | Example 4 | Comparative Example 5 | Example 4 |
| Recovery rate of protein | 80% | 82% | 72% | 80% |
| Recovery rate of Avicel degrading activity | 82% | 97% | 80% | 96% |
| Recovery rate of xylan degrading activity | 96% | 97% | 91% | 96% |
| Recovery rate of cellobiose degrading activity | 98% | 100% | 82% | 94% |

When the concentrated enzyme liquid obtained using only the ultrafiltration membrane with a molecular weight cut off of 30,000 in Comparative Example 5 was compared to the recovered enzyme liquid obtained by mixing the first concentrated enzyme liquid obtained using the ultrafiltration membrane with a molecular weight cut off of 100,000 with the second concentrated enzyme liquid obtained using the ultrafiltration membrane with a molecular weight cut off of 30,000 in Example 5, we found that the recovery rate of the protein increased more in Example 5 than in Comparative Example 4. In addition, we found that, in Example 5, the recovery rate of the Avicel degrading activity significantly increased in particular. We found that these tendencies were the same tendency as in the cases where the ultrafiltration membrane with a molecular weight cut off of 10,000 was used (Example 1 and Comparative Example 1).

INDUSTRIAL APPLICABILITY

The obtained cellulase can be effectively used in detergent application and applications such as hydrolysis of starch and hydrolysis of cellulose.

The invention claimed is:

1. A method of producing cellulase comprising a microcrystalline cellulose degrading activity, comprising steps (1) to (3):
   (1) subjecting an aqueous solution of cellulase derived from filamentous fungi to liquid-liquid filtration through an ultrafiltration membrane with a molecular weight cut off of 100,000 Da to 200,000 Da to obtain a filtrate and concurrently obtain a concentrated enzyme solution as a retentate;
   (2) further subjecting the filtrate obtained in step (1) to filtration through a second ultrafiltration membrane with a molecular weight cut off of 5,000 Da to 50,000 Da to obtain a second concentrated enzyme solution as a retentate; and
   (3) mixing the concentrated enzyme solution obtained in steps (1) and (2) to obtain cellulase comprising a microcrystalline cellulose degrading activity, derived from filamentous fungi.

2. The method according to claim 1, wherein said filamentous fungi are *Trichoderma*.

3. The method according to claim 1, wherein said aqueous solution of cellulase derived from filamentous fungi is adjusted to pH 2.6 to 5.4 or pH 8.6 to 9.4 in step (1).

4. The method according to claim 1, wherein said aqueous solution of cellulase derived from filamentous fungi is a filamentous fungi culture liquid or a hydrolysate of biomass containing cellulose obtained by using said cellulase derived from filamentous fungi.

5. The method according to claim 1, wherein said aqueous solution of cellulase derived from filamentous fungi comprises one or more enzyme components selected from the group consisting of cellobiohydrolase, endoglucanase, and xylanase.

6. The method according to claim 1, wherein a temperature of said aqueous solution of cellulase derived from filamentous fungi is 15 to 35° C.

7. The method according to claim 2, wherein said aqueous solution of cellulase derived from filamentous fungi is adjusted to pH 2.6 to 5.4 or pH 8.6 to 9.4 in step (1).

8. The method according to claim 2, wherein said aqueous solution of cellulase derived from filamentous fungi is a filamentous fungi culture liquid or a hydrolysate of biomass containing cellulose obtained by using said cellulase derived from filamentous fungi.

9. The method according to claim 3, wherein said aqueous solution of cellulase derived from filamentous fungi is a filamentous fungi culture liquid or a hydrolysate of biomass containing cellulose obtained by using said cellulase derived from filamentous fungi.

10. The method according to claim 2, wherein said aqueous solution of cellulase derived from filamentous fungi comprises one or more enzyme components selected from the group consisting of cellobiohydrolase, endoglucanase, and xylanase.

11. The method according to claim 3, wherein said aqueous solution of cellulase derived from filamentous fungi comprises one or more enzyme components selected from the group consisting of cellobiohydrolase, endoglucanase, and xylanase.

12. The method according to claim 4, wherein said aqueous solution of cellulase derived from filamentous fungi comprises one or more enzyme components selected from the group consisting of cellobiohydrolase, endoglucanase, and xylanase.

13. The method according to claim 2, wherein a temperature of said aqueous solution of cellulase derived from filamentous fungi is 15 to 35° C.

14. The method according to claim 3, wherein a temperature of said aqueous solution of cellulase derived from filamentous fungi is 15 to 35° C.

15. The method according to claim 4, wherein a temperature of said aqueous solution of cellulase derived from filamentous fungi is 15 to 35° C.

16. The method according to claim 5, wherein a temperature of said aqueous solution of cellulase derived from filamentous fungi is 15 to 35° C.

17. The method according to claim 1, wherein the filtrate and the retentate are both liquids in step (2).

18. A method of producing cellulase comprising a microcrystalline cellulose degrading activity, comprising
   an ultrafiltration step consisting of steps (1) and (2),
   (1) subjecting an aqueous solution of cellulase derived from filamentous fungi to liquid-liquid filtration through an ultrafiltration membrane with a molecular weight cut off of 100,000 Da to 200,000 Da to obtain a filtrate and concurrently obtain a concentrated enzyme solution as a retentate;
   (2) further subjecting the filtrate obtained in step (1) to filtration through a second ultrafiltration membrane with a molecular weight cut off of 5,000 Da to 50,000 Da to obtain a second concentrated enzyme solution as a retentate; and
   (3) mixing the concentrated enzyme solution obtained in steps (1) and (2) to obtain cellulase comprising a microcrystalline cellulose degrading activity, derived from filamentous fungi.

* * * * *